United States Patent [19]
Bireley

[11] Patent Number: 4,850,386
[45] Date of Patent: Jul. 25, 1989

[54] SOIL MOISTURE MONITOR

[75] Inventor: Richard L. Bireley, San Diego, Calif.

[73] Assignee: Aquametrics, Inc., San Diego, Calif.

[21] Appl. No.: 4,047

[22] Filed: Jan. 16, 1987

Related U.S. Application Data

[63] Continuation-in-part of Ser. No. 836,217, Feb. 28, 1986, abandoned, which is a continuation-in-part of Ser. No. 688,255, Jan. 2, 1985, abandoned.

[51] Int. Cl.⁴ .............................................. F16K 17/26
[52] U.S. Cl. ................... 137/78.3; 324/61 R; 324/61 QS; 324/61 P; 361/178; 361/181
[58] Field of Search ................. 324/61 R, 61 P, 65 P, 324/61 QS; 73/73; 361/178, 181, 188; 137/78.2, 78.3

[56] References Cited

U.S. PATENT DOCUMENTS

| | | | |
|---|---|---|---|
| 3,683,671 | 8/1972 | Van Swaay | 73/27 R |
| 3,793,585 | 2/1974 | Wilska | 324/61 QS |
| 3,870,951 | 3/1975 | Brown et al. | 324/61 P |
| 3,879,644 | 4/1975 | Maltby | 324/61 P |
| 3,882,381 | 5/1975 | Gregory | 324/61 R |
| 4,023,206 | 5/1977 | Nishibe et al. | 324/65 P |
| 4,137,931 | 2/1979 | Hasenbeck | 137/78.3 |
| 4,175,239 | 11/1979 | Sandler | 361/181 |

Primary Examiner—A. Michael Chambers
Attorney, Agent, or Firm—Ellsworth R. Roston; Charles H. Schwartz

[57] ABSTRACT

A monitor or sensor for sensing the moisture content of a surrounding medium comprises two electrodes connected in a detector circuit for detecting the impedance between them and producing an output signal proportional to the impedance. At least one of the electrodes is covered by a dielectric coating and the other electrode is positioned to minimize any capacitative effects between the electrodes through the surrounding medium. The detector may comprise a multivibrator with an output frequency controlled by the sensor impedance, and the output signal can be used to control the operation of watering equipment.

38 Claims, 2 Drawing Sheets

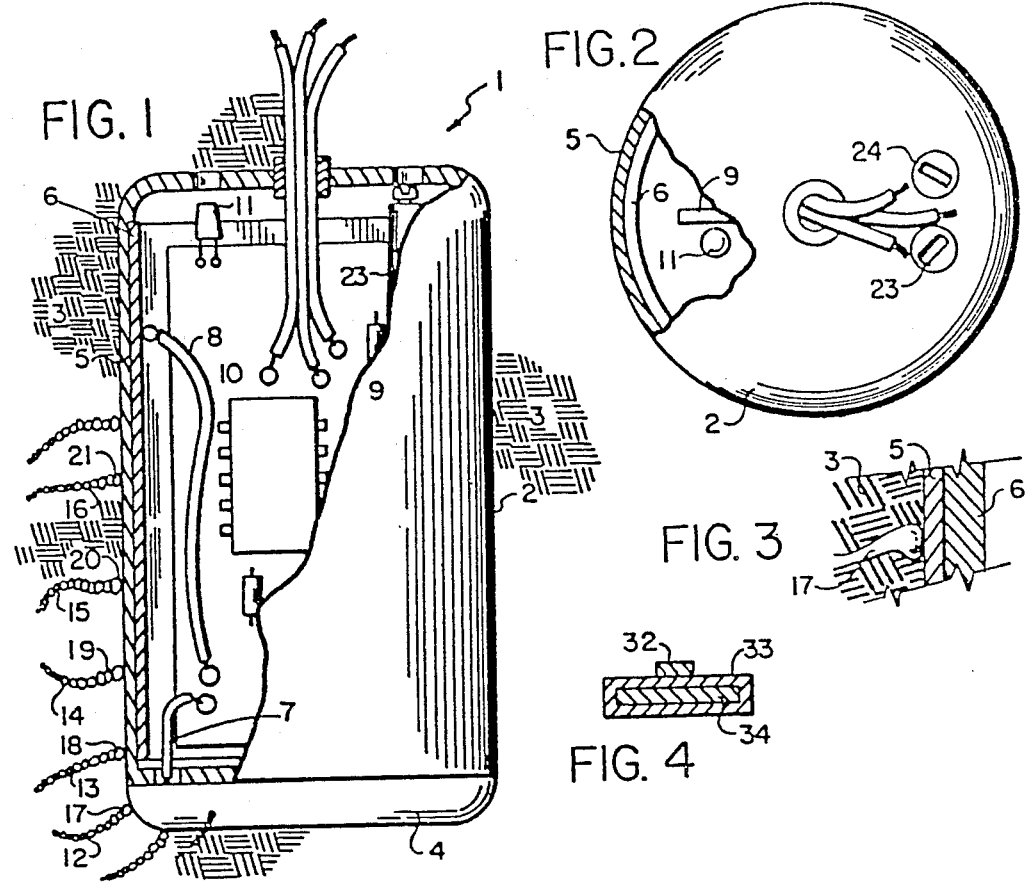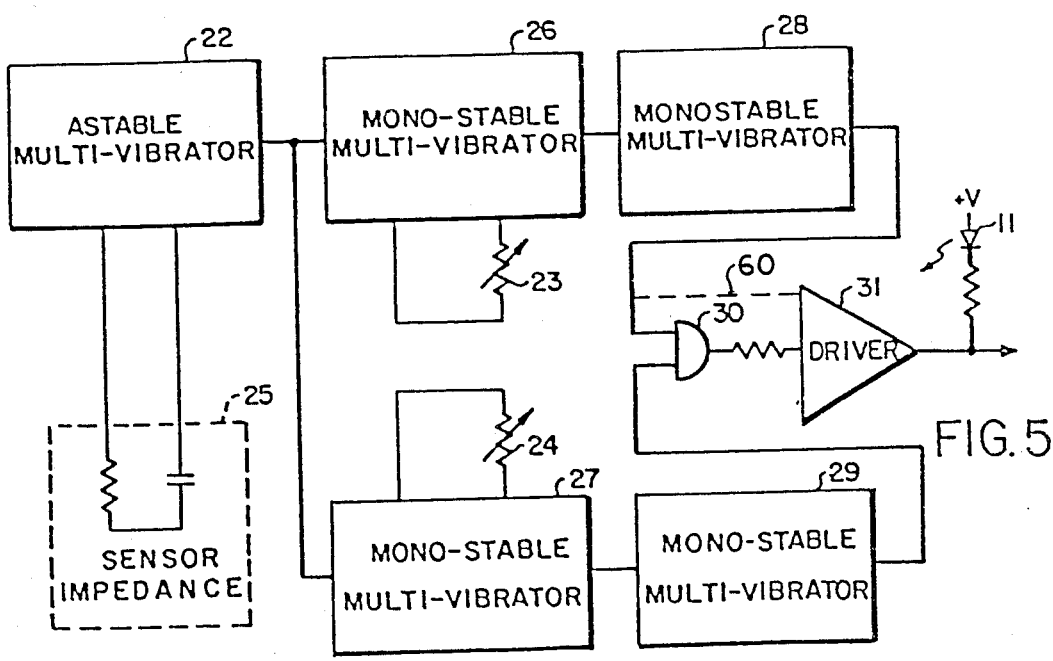

SOIL MOISTURE MONITOR

CROSS REFERENCE TO RELATED APPLICATIONS

This application is a Continuation-In-Part of my Application Ser. No. 836,217 filed Feb. 28, 1986, which was a Continuation-In-Part of Application Ser. No. 688,255 filed Jan. 2, 1985 both Application, now abandoned.

FIELD OF THE INVENTION

This invention relates to electronic fluid and moisture level monitors, or sensors for detecting the moisture level in a given medium such as soil. Such sensors are typically used in control of irrigation or watering equipment.

BACKGROUND OF THE INVENTION

Apparatuses for detecting and measuring the presence and level of fluid in a given medium are commonly used for monitoring and controlling fluid levels, flow, relative moisture contents, liquid spills, contamination and the like.

Contemporary sensor technology depends on changes in the dielectric property of the medium caused by variances in fluid level or fluid concentration within the medium. Sensors of contemporary design typically utilize a parallel plate capacitor immersed or embedded in the medium so that a portion of the medium may function as a dielectric between the plates. The capacitor is part of the RC circuit of an oscillator whose frequency varies with changes in the dielectric property of that portion of the medium between the plates. This technique is generally satisfactory when the dielectric-forming medium is a fluid; the gap between the plates can be narrow enough to yield a relatively high capacitance. However, when dealing with granular or pulverous media, a wider plate gap is necessary; and inaccuracies can be introduced by changes in the enclosed medium. Furthermore, as the fluid absorbing medium becomes increasingly saturated, the relationship between the dielectric value and fluid concentration becomes less linear. As a consequence, accuracy of fluid concentration measurement suffers.

Another problem of relying on changes in the dielectric properties of a surrounding medium is that impurities contained in the water produce significant changes in the dielectric constant which are not easily determined. Thus, the presence of salts will produce the same effective capacitance as a larger volume of water.

By accurately monitoring moisture levels in cultivated land in order to provide optimum irrigation, significant gains can be achieved in water and energy conservation. The control of sprinklers, pumps and other irrigation equipment from moisture monitors embedded at plant root-level has almost become a necessity in the water-poor sun-belt western states.

Conventional moisture sensors of the type described above are not only inaccurate under certain conditions, but are difficult to embed in the ground due to their fragile plate configuration and internal electronic components. There is a need for a more sensitive type of soil moisture monitor packaged in an easily embedded, durable, compact enclosure.

SUMMARY OF THE INVENTION

It is an object of the present invention to provide a soil moisture monitor which is designed to minimize or eliminate the effects of changes in the dielectric constant of a surrounding medium. This can be done by suitable design of the electrodes and by suitable arrangement of the oscillator circuit.

According to the present invention a solid moisture monitor is provided which comprises two electrodes and a detector circuit connected to the electrodes to measure the impedance between them. At least one of the electrodes is enclosed in an insulating dielectric coating having a fixed dielectric constant. The second electrode is positioned relative to the first electrode so as to minimize or avoid any capacitative effects between the two electrodes through a surrounding medium. Thus there is no material, other than the dielectric coating, between the two electrodes. The detector circuit is also designed to have an operating frequency low enough to minimize capacitative effects of the surrounding medium, i.e. so that is no significant field is built by the device into the surrounding medium.

In the preferred arrangement, the detector circuit is an oscillator circuit designed to have an operating frequency no greater than 20 KHz. The reactance is determined by the equation:

$$X_c = \frac{1}{2\pi f c}$$

where $X_c$ is the reactance of the circuit, f is the frequency and c is the capacitance. Thus, the lower the frequency is, the higher the reactance will be. For higher frequencies, the circuits reactance will be lower and thus the effect of the reactance of the surrounding medium on the circuit operation will be greater.

The oscillating frequency of the circuit will be determined in part by the impedance between the two electrodes. This impedance will be determined by the unchanging dielectric constant of the material covering at least one of the electrodes, and the total surface area of the water droplets in contact with the surface of the material between the two electrodes. The electrodes are preferably situated relatively close together to reduce the resistance of the water droplet paths, the number of which will be proportional to the moisture level of the surrounding material.

Thus the apparatus can be designed for embedding in a granular material such as soil to measure its moisture content in a manner substantially independent from the dielectric constant of the material.

Traces or paths of water will form between the first electrode and the hydrophobic dielectric coating or layer of the second electrode. The impedance between the electrodes will therefore vary according to the moisture level of the soil, since the number of water paths or traces will increase as the moisture level increases. This substantially eliminates or minimizes the effects of changes in the dielectric constant of the surrounding medium, since the traces of water contacting the dielectric coating of the second electrode act as one slate of a point capacitor, with the insulator acting as the dielectric and having the second electrode as their common plate. The capacitance will therefore be a function of the number of water traces between the first electrode and the dielectric layer and the thickness and dielectric constant of the cielectric layer. The capacitance will rise with increasing moisture content to a maximum value determined by the area of the insulated electrode.

The geometry and relative positioning of the two electrodes is chosen so that the sensor can be easily embedded in the material such as soil and so that the effect of the dielectric constant of the surrounding material is minimized —i.e. no significant capacitive effects occur directly between the two electrodes through the soil or other surrounding material. This can be done, for example, by arranging the electrodes at a sufficient spacing to minimize such effects or by placing the first electrode on the exposed surface of the dielectric coating layer of the second electrode, so that the capacitance between the plates is only through the dielectric layer which has a fixed dielectric constant.

In another arrangement, the two electrodes may be arranged side by side within an insulating coating covering both electrodes so that conductive paths of water droplets can be formed between positions on the coating covering the two electrodes. These will form series capacitors through the dielectric coating to the respective underlying electroce.

Due to the lower dielectric constant of the insulating or dielectric coating, as well as the controlled thickness of the coating, the point capacitances formed by the water droplets through the dielectric coating show a significantly higher impedance than any undesirable capacitance established through the surrounding medium. As a result, the effect of these stray capacitances is minimized, as well as the effects of impurities in the solution.

In the preferred embodiment of the invention the sensor forms the reactive component for controlling the frequency of an a stable multivibrator or other oscillator whose output frequency varies according to the impedance of the sensor, and thus according to the moisture level of the surrounding material. As the moisture level goes up, the number of conductive paths increases, and the sensor capacitance increases so that the resultant oscillator output frequency drops.

A suitable frequency detection circuit may be provide to detect the output frequency and produce a control signal if it rises above a predetermined level corresponding to a predetermined moisture level at which sprinklers are to be operated. The control signal can be used to turn on sprinkling or irrigation equipment, for example, and a timer or further control signal produced when the frequency falls below a further predetermined threshold maybe used to turn off the equipment.

The sensor in the preferred embodiment is a flat, strip like device which can be easily embedded in the soil, and is preferably connected to a remote detector circuit to allow the moisture level to be monitored easily.

The aforementioned technique provides a highly accurate sensor due to the high value of capacitance which results from the summing of the various point capacitances, and the minimizing of the changes in the surrounding medium.

BRIEF DESCRIPTION OF THE DRAWINGS

The present invention will be better understood from the following detailed description of some preferred embodiments of the invention, taken in conjunction with the accompanying drawings in which like reference numerals refer to like parts, and in which:

FIG. 1 is a front elevational view of a soil moisture sensor according to one embodiment of the invention with a section of the wall cut away to show the internal configuration;

FIG. 2 is a top plan view of the sensor;

FIG. 3 is a diagrammatic al interpretation of the point of contact between a water droplet and the dielectric coated electrode;

FIG. 4 is a cross-sectional view of a sensor in an alternative embodiment;

FIG. 5 is an electrical diagram of the sensor circuitry;

DESCRIPTION OF THE PREFERRED EMBODIMENTS OF THE INVENTION

Figure 6:
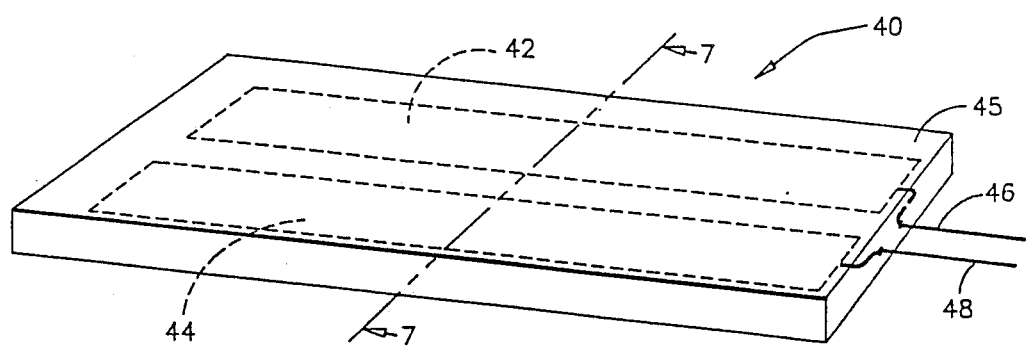
FIG. 6 is a perspective view of a sensor according to another embodiment of the invention.

A first embodiment of the invention is illustrated in FIGS. 1, 2, 3 and 5 of the drawings.

Referring now to FIG. 1, a soil moisture sensor 1, packaged in a generally cylindrical enclosure 2, is embedded in a porous plant-growing medium 3 preferably at root level. A first, exposed electrode 4, comprises the bottom of enclosure 2. A second, insulated electrode 6 comprises the cylindrical wall of enclosure 2 and is coated on its exposed cylindrical surface by a thin layer of hydrophobic, dcielectric material 5 such as glass, porcelain or other vitreous compound, a synthetic resin polymer (e.g. polytetrafluoroethylene) or a thermosetting resin (e.g. One of the polymerized epoxides).

Insulated wires 7 and 8 respectively connect exposed electrode 4 and insulated electrode 6 to a printed circuit board 9 carrying control circuitry of the sensor which is described in more detail below in connection with FIG. 5.

The two electrodes 4 and 6 together make up a complex impedance dependent on the moisture level of the surrounding medium 3. Traces or droplets of water containing dissolved impurities will be present in the medium 3 to an extent dependent on the moisture level, and these traces will contact one another to form conducting paths between electrode (4) and the dielectric coating as generally illustrated at 12, 13, 14 and 15 in FIG. 1 between the exposed electrode 4 and the insulated electroce 6. These paths are only partially shown in FIG. 1 for reasons of clarity but each droplet path will in practice form a continuous trace from one electrode to the other. Point capacitances are formed at the point 17, 18, 19, 20 and 21 at which each droplet path touches the dielectric layer 5 between those points and the opposing portions of the insulated electrode 6 as the opposite plate. The number of capacitors formed by such droplets will increase as the moisture level increases, thus increasing the overall capacitance of the sensor, effectively swamping any effects of the dielectric constant of the surrounding medium. The complex impedance formed between the water droplets electrode thus functions as an RC circuit, as indicated in FIG. 5, with the capacitance related to the sum of all droplet point capacitances and the small resistance related to the resistive factor introduced by the conductive paths created by the water droplets laden with dissolved impurities. As previously stated, the effect of the resistive factor is minimized through choice of geometry and frequency. This impedance will be directly related to the moisture level in the surrounding medium, and can be used in a suitable detector circuit to produce an output proportional to the moisture level.

The sensor is arranged to eliminate or minimize the effects of changes in the dielectric constant of the surrounding medium with changing moisture level. This is done be designing the electrodes to avoid or minimize any capacitive effects between the electrodes through the surrounding medium, and by arranging the operating voltage and frequency of the detector circuitry to minimize any build up of a field into the surrounding medium. This maximizes the effect of the impedance formed between the droplet points on the outer surface of the dielectric layer and through the dielectric layer to the insulated electrode. Thus, there is substantially no capacitive effect taking place between the electrodes through the surrounding medium itself, and the major impedance between the electrodes is only through the dielectric layer which has a fixed dielectric constant. Thus the effect of increasing moisture level in the material surrounding the sensor is found to be substantially linear, and becomes more linear as the saturation level approaches 100 percent. This is unlike previous sensor arrangements where both electrodes are exposed to the surrounding medium, so that the sensor is liable to become less linear as the moisture level reaches saturation.

In the embodiment of FIG. 1, capacitative effects between the electrodes are minimized by the non facing arrangement of the electrodes. The detector circuit operating characteristics will now be explained.

The complex impedance of the sensor determines the vibration frequency of an a stable multivibrator 22. As the moisture level of the soil increases, the resulting increase in the number of point capacitances forming on the coated electrode 6 causes a drop in the oscillation frequency of a stable multivibrator 22. A potentiometer 23 can be adjusted to set the multivibrator frequency level at which a solenoid driver circuit is activated and deactivated, as described below.

The sensor is designed specifically so that changes in dielectric constant of the surrounding medium have a minimal effect. By making the multivibrator frequency relatively low, suitably in the 20 KHz range or lower, and the thickness of the dielectric relatively high, preferably in the 5–10 mm range, so that ehs sensor reactance is also relatively high compared to that of the medium, the effect of changes in reactance of the surrounding medium is effectively swamped or minimized and the reactance of the sensor will dominate. The operating voltage of the circuit of FIG. 5 is preferably below 12 volts, and is of the order of 8 volts in the preferred embodiment. The frequency and dielectric thickness may be modified in alternative embodiments while maintaining the desired relative relationship between the sensor and surrounding medium reactance.

As shown in FIG. 5, the electrodes 4 and 6 forming the sensor impedance 25 which functions as an RC circuit are connected to a stable multivibrator 22 so as to determine the oscillation frequency of the multivibrator. The multivibrator is provided on chip 10 which is mounted on the printed circuit board 9 as shown in FIG. 1.

The multivibrator 22 has its output connected to a first monostable multivibrator 26 which functions as a frequency discriminator with a threshold determined by the setting of potentiometer 23. The output of multivibrator 26 is connected to the input of a second monostable multivibrator 28 which functions as a filter. The inverted or Q output of the second monostable 28 is connected to one input of AND gate 30. Gate 30 has its output connected to solenoid driver circuit 31 which is connected to a light switching diode 11. Diode 11 is mounted on the printed circuit board 9 so as to be visible through a window in enclosure 2 and will light up when circuit 31 is activated.

The output of a stable multivibrator 22 in the illustrated embodiment is also connected through a timing circuit consisting of monostable multivibrator 27 with its threshold determined by the setting of potentiometer 24, and a further monostable multivibrator 29 connected to the output of the first monostable 27 and having its inverted or $\overline{Q}$ output connected to AND gate 30.

Multivibrators 27 and 29 are connected in the non-retriggerable mode and are set to time out at a predetermined interval, as described in more detail below. The multivibrators 27 and 29 and AND gate 30 are not essential to the operation of the circuit and are inserted to provide an arbitrarily long overriding shut off interval, as described below. Thus in an alternative, simplified embodiment the $\overline{Q}$ terminal of multivibrator 28 is connected directly to solenoid driver 31, as indicated by dotted lines in FIG. 5, and multivibrators 27 and 29, together with AND gate 30 may be eliminated from the circuit.

The operation of the basic circuit without multivibrators 27 and 29 and AND gate 30 will first be described.

The timing cycle of monostable multivibrator 26, which is connected in the retriggerable mode, is adjustable by means of potentiometer 23. Thus potentiometer 23 can be set for triggering the circuit when the moisture level falls below a minimum threshold (DRY mode).

WET mode operation of the circuit will first be described. If the moisture level is above the minimum threshold, the pulse output of astable multivibrator 22 will have a period exceeding that of monostable multivibrator 26 (set by potentiometer 23). Thus monostable 26 will be allowed to time out during each cycle, and is then retriggered to produce a pulsed output to monostable multivibrator 28 which triggers it into the HIGH conoition. This produces a low output at the $\overline{Q}$ terminal which holds the power triac 31 in an OFF mode.

As the moisture level drops below the minimum threshold set by potentiometer 23, the period of the pulsed output from astable multivibrator 22 decreases until it is less than that of monostable 26. At this point the circuit 26 is not allowed to time out and a steady state high output is produced. Therefore, no triggering pulse is applied to monostable 28 and it will be held in the low, reset mode. Thus, its $\overline{Q}$, inverted output will be high. At this point the power triac or driver 31 will be turned to the ON state.

Driver 31 is designed to control solenoid-controlled valves of the type commonly used with watering or irrigation equipment. Thus as soon as the moisture level falls below the predetermined minimum threshold, the watering equipment is turned on.

Alternatively, the multivibrator 28 can be directly connected to the driver 31. This is indicated by broken lines at 60 in FIG. 1. In this alternative arrangement, and AND gate 30 is not included and the mono-stable multivibrator 29 provides no control over the operation of the driver 31.

The watering cycle may be controlled to be switched off after a fixed interval of watering time each time the monostable 28 produces a high output at its $\overline{Q}$ terminal. Alternatively, the monostables 26 and 28 could be arranged such that the watering equipment is started at fixed intervals and shut-off only when a maximum desirable water level is reached. In this case potentiometer 23 would be set such that monostable 26 is allowed to time out to trigger monostable 28 into a high condition only when the output period of astable multivibrator 22 exceeds a value corresponding to the maximum desired water level. The resultant low output at the $\overline{Q}$ terminal of monostable 28 could then be used to turn the watering equipment off. Thus the frequency discriminating upper part of the circuit shown in FIG. 5 can be arranged to turn watering equipment on when the minimum tolerable moisture level is reached or to turn the equipment off when a maximum desirable water saturation is reached. When used in either mode, a considerable conservation of water may be achieved while maintaining ground moisture within an optimum range.

The light emitting diode 11 is provided to aid in adjustment of potentiometers 23 and 24. Both the potentiometers and the diode are accessible through sealable holes in the top of enclosure 2. Thus, for example, the sensor can be calibrated for a desired moisture level by adding controlled quantities of moisture to the surrounding medium and adjusting potentiometer 23 so that the light goes off when the desired moisture level is reached. The moisture threshold, whether set up for a minimum or maximum moisture level, can be adjusted both in the field and during manufacture, as desired.

The operation of the full circuit including the timing circuit and AND gate 30 shown in FIG. 5 will now be described. As mentioned above, these circuit components are not essential to operation of the device but are provided only as an optional modification for reducing water run off losses.

In the circuit shown in FIG. 5 the output of AND gate 30 will be high only if both inputs are high. Thus, if the moisture level falls below the threshold set by potentiometer 23 and the $\overline{Q}$ terminal of multivibrator 28 goes high, the watering equipment will be switched on only if the input from multivibrator 29 is also high.

Monostable multivibrators 27 and 29 are set by potentiometer 24 into a nonretriggerable mode where multivibrator 27 has predetermined pulsed output which goes high at predetermined fixed intervals, setting the next multivibrator high for a fixed interval so that its $\overline{Q}$ output goes low for that period. This will hold the solenoid driver off for a fixed interval even if the output of multivibrator 28 is high. The next time the $\overline{Q}$ output of multivibrator 29 goes high, the watering equipment will be turned on for a fixed interval, then off again, then on again, and so on until the moisture level again rises above the threshold level so that the $\overline{Q}$ output of multivibrator 28 is low.

The periodic time outs of the watering cycle introduced by the multivibrators 27 and 29 will allow time for water to percolate into the soil, thus reducing run off losses significantly. The time interval can be set according to the time estimated to be necessary to allow full water percolation. For example, time outs of the order of 2 minutes may be set in a typical application. Thus, with the full circuit operating as shown in FIG. 5, each time the solenoid diver is triggered ON by simultaneous high inputs to AND gate 30, it will be periodically triggered OFF again for repeated predetermined intervals by the timing out of multivibrator 29 to allow time for water percolation, until the point at which the moisture level again rises above the minimum level so that the other input to AND gate 30 goes low to hold the driver OFF.

The optional connection of the $\overline{Q}$ output of multivibrator 28 directly to the solenoid driver 30, eliminating the periodic time outs, is illustrated in dotted lines on FIG. 5. Clearly alternative timing means may be provided if desired to provide time outs in the watering cycle. If required, provision may be made for the insertion of some hysteresis in the frequency discriminator part of the circuit, for the reduction or prevention of solenoid chatter at the set point or threshold.

The relative configuration and geometry of the two electrodes of sensor 1 need not be s shown in FIG. 1, but is chosen so as to minimize the effects of changes in the dielectric constant of the surrounding medium while producing a sensor of sufficient rigidity for easy embedding in the medium. Ease of manufacture is also a factor in choice of electrode configuration.

The electrode arrangement is preferably such that the impedance factor introduced by the resistance of the conductive paths through the medium 3 between the exposed electrode and the insulated electrode is considerably less than the impedance produced by the point capacitors formed on the insulated electrode at the end of the conductive paths. This means that the electrodes should not be too far apart, so that the resistive factor can be arranged to be insignificant as compared to the capacitive factor and the total effective impedance varies substantially linearly with the moisture level of the soil, with the linearity increasing with increasing moisture content. This can be done both by minimizing the conductive path length from the exposed electrode to the insulated electrode, and by providing a relatively large exposed area of the insulated covering of the insulated electrode for formation of point capacitances. Direct capacitance between the electrodes through the dielectric or insulating layer is also minimized in the preferred embodiments, and is swamped by the effects of the point capacitances formed by the water droplet paths.

Figure 7:
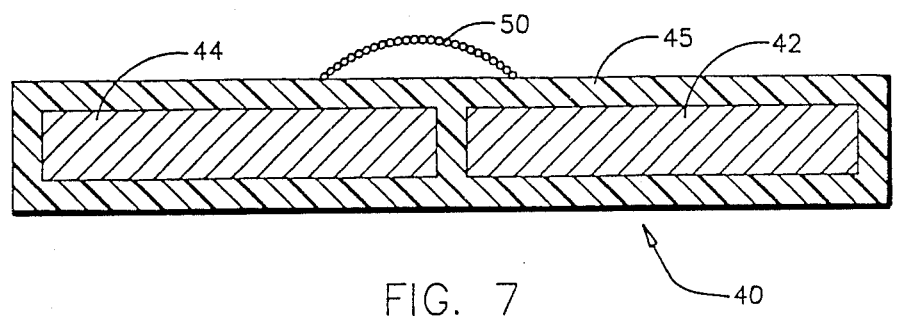
FIG. 7 is a cross-section on the lines 7—7 of FIG. 6.

FIGS. 4, 6 and 7 show a possible alternative electrode configurations for the sensor. In each of these embodiments the electrodes will be connected in the circuit of FIG. 5 and will function in the manner described above.

In FIG. 4 insulated electrode 34 is covered by an insulating or dielectric coating 33 wrth exposed electrode 32 provided as a thin metal strip applied to the outer surface of coating 33 so as to leave the major area of the coating exposed to the surrounding material. The sensor assembly may itself be in the form of a thin strip which projects at one end into a housing containing the frequency discriminating circuitry (not shown). Alternatively, wiring may be provided for connecting the electrode to remote detector circuitry. The sensor of FIG. 4 operates in the same manner as described above to respond to conductive water droplet paths formed between the exposed faces of electrode 32 and layer 33.

In another alternative arrangement, the insulated electrode may be split in two with the exposed electrode coplanar with and sandwiched between the resultant two insulated electrode halves.

Another alternative electrode configuration for the sensor is shown in FIGS. 6 and 7. As shown in FIGS. 6 and 7, electrode assembly 40 comprises a pair of flat, striplike electrodes 42, 44 extending side by side with a small gap 46 between them. The electrooes are embedded in an envelope 45 of a suitable dielectric material, such as polyethylene or the like. The entire envelope strip is very thin, suitably of the order of credit card thickness, so that it can easily be embedded in a material, such as soil, to measure the moisture content. The electrodes may comprise thin strips of copper or equivalent materials.

The two electrodes are connected via leads 46, 48 in a remote detector circuit as shown in FIG. 5. Thus the entire detector circuit does not have to be embedded in the ground with the electrode assembly.

By arranging the electrodes with a large, dielectric covered area facing the surrounding medium and only a relatively small area of the electrodes facing one another across the small gap 46, as well as having the oscillator operating frequency very low, as described above the effect of the changes in the dielectric constant of the surrounding medium will be swamped or minimized as will any direct capacitance between the two electrodes. Water droplet paths 50 will form from points on the envelope above one electroce to points directly above the other electroce, as indicated in FIG. 7. The number of paths 50 will depend on the moisture content of the surrounding material. Point capacitances are formed at the points each croplet path touches the dielectric envelope, between the respective points and the opposing portions of the respective underlying electrode. Thus each droplet will have the effect of two capacitors connected in series with a resistance dependent on the water droplet conductive path. As in the previous embodiments, the resultant complex impedance connected in the oscillator circuit of FIG. 5 will determine the vibration frequency of astable multivibrator 22. As the moisture level goes up, the number of series connected point capacitors increases and the output frequency of the astable multivibrator goes down.

The moisture monitor with an electrode configuration as shown in FIGS. 6 and 7 will therefore operate in the same way as described above connection with FIG. 5, to give an output indicative of the moisture content of the surrounding material. Because of its thin, striplike form, it can easily be embedded in soil, for example, without having to dig out a hole first, and can be moved from one place to another to test for uniform watering.

Thus, the soil moisture monitors with electrode configurations as explained above are all designed to minimize the effects of changes in the dielectric constant of the surrounding medium by substantially reducing or avoiding any capacitance between the electrodes through the surrounding medium. At the same time, the effects of point capacitances formed via water droplet paths between the electrodes are maximized to swamp any effects of the dielectric constant of the surrounding medium. At least one electrode is enclosed or insulated from the surrounding medium, while the electrodes are preferably physically close together either in a non-facing relationship or with only a dielectric layer of fixed dielectric constant between them. The electrodes are connected in an oscillator circuit for controlling the output frequency according to moisture level, and the oscillator operating frequency is 20 KHz or less to minimize the build up of any field into the surrounding medium.

While the preferred embodiment of the invention has been disclosed, other embodiments may be devised and modifications made within the spirit of the invention and within the scope of the appended claims.

What is claimed is:

1. In combination for disposition in the earth to determine the moisture in the earth,
    a first conductive electrode defining first plates of capacitances,
    a dielectric material covering the first electrode to define the dielectric material of the capacitances, and
    a second electrode disposed relative to the first electrode and the dielectric material to provide isolated paths through the moisture in the earth to the dielectric material in accordance with the relative amount of the moisture in the earth and to estabish, at the dielectric material, the paths to the dielectric material as the second plates of the capacitances.

2. In a combination as set forth in claim 1,
    the second electrode being displaced from the first electrode and the dielectric material in transverse relationship to the first electrode end the dielectric material to assure that the second electrode does not establish a capacitance with the first electrode.

3. In a combination as set forth in claim 1,
    watering means having a first and second states of operation and operative in the first state to provide a watering of the earth and operative in the second state to prevent watering of the earth, and
    means responsive to the values of the impedances of the capacitances for controlling the operation of the watering means in the first and second states in accordance with such impedance values.

4. In a combination as set forth in claim 2,
    watering means having a first and second states of operation and operative in the first state to provide for a watering of the earth and operative in the second state to prevent a watering of the earth,
    means responsive to capacitance values less than a first particular value in the capacitances for providing an operation of the watering means in the first state, and
    means responsive to capacitance values greater than a second particular value for providing an operation of the watering means in the second state where the second particular value is greater than the first particular value.

5. In a combination as set forth in claim 1,
    watering means having first and second states of operation and operative in the first state to provide for a watering of the earth and operative in the second state to prevent a watering of the earth,
    means responsive to a value in the capacitances less than a particular value for operating the watering means in the first state, and
    means responsive to an operation of the watering means in the first state for a particular period of time to obtain an operation of the watering means in the second state.

6. In combination for disposition in the earth to determine the moisture in the earth,
    a housing,
    a first electrode disposed within the housing to define a first plate of capacitances,
    a dielectric material covering the first electrode to define the dielectric in the capacitances,
    a second electrode disposed relative to the first electrode to inhibit any capacitive effects between the first and second electrodes and to provide for the formation of conductive paths from the second electrode through the moisture in the earth to the dielectric material to define the second plates of the capacitances, and
    means for producing a voltage difference between the first and second electrodes.

7. In a combination as set forth in claim 6 wherein the first electrode is disposed in a substantially vertical position in the housing and the second electrode is disposed in substantially a horizontal position in the housing.

8. In a combination as set forth in claim 6 for energizing a source of water,
means responsive to the capacitances values provided by the capacitances for energizing the source of water when the value of the capacitances has declined below a particular value.

9. In a combination as set forth in claim 8 for energizing a source of water,
means responsive to the values of the capacitances for energizing the water source when such values are less than a first particular value, and
means operative upon the energizing of the watering source for de-energizing the watering source upon the earlier to occur of a second particular value in the capacitances and a particular time after the energizing of the watering source, the second particular value in the capacitances being greater than the first particular value in the capacitances.

10. In a combination as set forth in claim 9,
the housing being electrically non-conductive and constituting the dielectric material, and
means defining an oscillator with the capacitances to provide signals at a frequency dependent upon the value of the capacitances,
the energizing means and the de-energizing means for the water source being operative in accordance with the frequency of the signals from the oscillator means.

11. In combination for disposition in the earth determine the moisture in the earth,
first and second thin conductive layers having a planar configuration and disposed in adjacent relationship to define first plates of first and second capacitances,
a dielectric material covering the first and second thin conductive layers and defining the dielectric in the first and second capacitances,
the moisture in the earth defining the second plates of the first and second capacitances and defining the connections between the second plates in the first capacitances and the second plates in the second capacitances, and
means for introducing an energizing voltage between the first and second thin conductive layers.

12. In a combination as set forth in claim 11,
the first and second conductive layers being co-planar and the dielectric material on the first and second conductive layers being thin and substantially uniform.

13. In a combination as set forth in claim 11,
means responsive to the values of the first and second capacitances for producing signals having a variable frequency in accordance with variations in such values, and
means responsive to the variations in the signal frequency for providing a controlled watering of the earth.

14. In a combination as set forth in claim 13,
means responsive to a first frequency of a relatively high value in the signal for providing for a watering of the earth, and
means responsive to a second frequency of a lower value than the first frequency for discontinuing the watering of the earth.

15. In a combination as set forth in claim 13,
means responsive to a first frequency in the signals of a relatively high value for providing for a watering of the earth, and
means operative upon an initiation of a watering of the earth for discontinuing the watering of the earth upon the earlier to occur of a fixed time interval or signals of a second frequency lower in value than the first frequency.

16. In combination for disposition in the earth to determine the moisture of the earth,
a thin conductive layer defining the first plates of capacitances,
a thin dielectric layer covering the thin conductive layer and defining the dielectric in the capacitances,
moisture in the earth defining the second plates of the capacitance, the number of the capacitances being dependent upon the amount of moisture in the earth,
conductive terminal means disposed relative to the thin conductive layer to inhibit any capacitive relationship with the thin conductive layer and to provide a terminal for the moisture defining the second plates in the capacitances, and
means for applying a voltage between the thin conductive layer and the terminal means.

17. In a combination as set forth in claim 16,
the thin conductive layer being conductive and the thin dielectric layer being uniformly disposed on the thin conductive layer.

18. In a combination as set forth in claim 16,
a second conductive layer disposed in relatively close relationship to the first conductive layer,
a second dielectric layer disposed on the second conductive layer,
the moisture in the earth defining second plates in second capacitances with the second conductive layer as the first plate in the second capacitances,
the voltage means applying the voltage between the first and second conductive layers.

19. In a combination as set forth in claim 18,
the first and second conductive layers being co-planar and the first and second dielectric layers being substantially uniform.

20. In a combination as set forth in claim 18,
means responsive to a particular value for the first and second capacitances for obtaining a watering of the earth.

21. In combination for obtaining a controlled watering of a patch of earth,
means for sensing the amount of moisture in the earth,
watering means having energized and de-energized states and operative in the energixzed state to water the patch of earth,
means responsive to the amount of moisture sensed in the earth for energizing the watering means when the amount of moisture in the patch of earth has fallen below a first particular value, and
means responsive to the energizing of the watering means for discontinuing the energizing of the watering means upon the earlier to occur of a particular time interval after such energizing and a second particular amount of moisture in the patch of earth, the second particular amount of moisture being greater than the first particular amount of moisture.

22. In a combination as set forth in claim 21, means operatively coupled to the sensing means for producing signals having a variable frequency in accordance with the output from the sensing means, the energizing means being perative upon the occurrence of signals of a particular frequency from the signal generating means.

23. In a combination as set forth in claim 22, the sensing means including parallel capacitances with the water in the patch of earth consititing one plate of such capacitance and the capacitances having a substantially constant dielectric.

24. In a combination as set forth in claim 23, the sensing means including a plurality of parallel capacitances each having a common first plate and each having second plates defined by moisture in the patch of earth, the plates in each capacitance being separated by a substantially uniform dielectric.

25. In a combination as set forth in claim 22, the sensing means being responsive to the amount of moisture in the patch of earth to provide a variable capacitance and the signal means being responsive to the variable capacitance to provide the variable frequency, the discontinuing means being operative upon the occurrence of a second particular frequency lower than the first particular frequency.

26. In combination for disposition in the earth to determine the moisture in the earth, a conductive electrode, a dielectric material on the conductive electrode, the moisture in the earth defining a number of parallel capacitances with the conductive electrode and the dielectric material, the number of parallel capacitances being dependent upon the amount of moisture in the earth, and dependent upon the amount of moisture in the earth, and conductive means disposed relative to the conductive electrode to inhibit the formation of a capacitance with the conductive electrode, the moisture in the earth establishing continuity between the conductive means and the conductive electrode.

27. In a combination as set forth in claim 26, means for applying a voltage between the conductive electrode and the conductive means.

28. In a combination as set forth in claim 26, means including the parallel capacitances for providing for a watering of the earth upon the occurrence of a particular value in the parallel capacitances.

29. In a combination as set forth in claim 28, means including the parallel capacitances for providing for discontinuance of the watering of the earth upon the occurrence in the parallel capacitances of a second particular value greater than the first particular value.

30. In a combination as set forth in claim 26, a second conductive electrode disposed in adjacent relationship to the first conductive electrode, a dielectric material on the second conductive electrode, the moisture in the earth defining a number of parallel capacitances with the second conductive electrode and the dielectric material, the number of such parallel capacitance being dependent upon the amount of moisture in the earth, the moisture in the earth further defining a series relationship between the parallel capacitance including the first conductive electrode and the parallel capacitances including the second conductive electrode, and means for applying a voltage between the first and second conductive electrodes.

31. In a combination as set forth in claim 30, the first and second conductive electrodes being coplanar and the dielectric material being uniformly disposed on the first and second conductive layers.

32. In a combination as set forth in claim 1, the paths through the moisture in the earth to the dielectric material being resistive, the impedances produced by the capacitances being considerably greater than the resistance in such moisture paths.

33. In a combination as set forth in claim 8, the conductive paths being resistive and the impedance produced by the capacitances being considerably greater than the resistances of such conductive paths.

34. In a combination as set forth in claim 13, the moisture defining the connections between the second plates in the first capacitances and the second plates in the second capacitances having a resistance considerably less than the impedances provided by the first and second capacitances.

35. In a combination as recited in claim 17, the moisture in the earth between the thin dielectric layer and the terminal means having a resistance considerably less than impedances provided by the capacitances.

36. A method of providing a controlled watering of plants in a patch of earth, including the steps of:

providing a sensor including a first electrode and a dielectric material covering the first electrode, disposing the sensor in the earth at a depth corresponding substantially to the depth of the roots of the plants in the patch of earth to obtain the formation of a number of parallel capacitances with the moisture in the soil adjacent the roots defining a first plate of the capacitances and the first electrode defining a common second plate for the capacitances, the number such capacitances being dependent upon the amount of moisture in the patch of earth, and providing for a watering of the patch of earth when the parallel capacitances reach a particular value.

37. A method as forth in claim 36, including the step of, providing for a discontinuance of the watering of the patch of earth when the parallel capacitance reach a second particular value greater than the first particular value.

38. A method as set forth in claim 36, including the step of:

providing for a discontinuance of the watering of the patch of earth when the earlier of the following occurs;

(a) a particular time has elapsed after the watering of the patch of earth has commenced or (b) the parallel capacitances reach a second particular value greater than the first particular value.

* * * * *